(12) United States Patent
Ma et al.

(10) Patent No.: US 10,232,036 B2
(45) Date of Patent: Mar. 19, 2019

(54) VACCINE FORMULATION, PREPARATION METHOD THEREFOR AND USE THEREOF

(71) Applicant: INSTITUTE OF PROCESS ENGINEERING, CHINESE ACADEMY OF SCIENCES, Beijing (CN)

(72) Inventors: Guanghui Ma, Beijing (CN); Wei Wei, Beijing (CN); Dezhi Ni, Beijing (CN); Hua Yue, Beijing (CN); Weiqing Zhou, Beijing (CN); Piping Lv, Beijing (CN)

(73) Assignee: INSTITUTE OF PROCESS ENGINEERING, CHINESE ACADEMY OF SCIENCES (CN)

( * ) Notice: Subject to any disclaimer, the term of this patent is extended or adjusted under 35 U.S.C. 154(b) by 0 days.

(21) Appl. No.: 15/563,660

(22) PCT Filed: Nov. 18, 2015

(86) PCT No.: PCT/CN2015/094878
§ 371 (c)(1),
(2) Date: Oct. 2, 2017

(87) PCT Pub. No.: WO2016/155325
PCT Pub. Date: Oct. 6, 2016

(65) Prior Publication Data
US 2018/0078635 A1 Mar. 22, 2018

(30) Foreign Application Priority Data

Apr. 2, 2015 (CN) .......................... 2015 1 0152994

(51) Int. Cl.
| | |
|---|---|
| *A61K 39/02* | (2006.01) |
| *A61K 49/00* | (2006.01) |
| *A61K 39/00* | (2006.01) |
| *A61K 39/29* | (2006.01) |
| *A61K 47/46* | (2006.01) |
| *A61K 31/7028* | (2006.01) |
| *A61K 38/20* | (2006.01) |
| *C12N 7/00* | (2006.01) |
| *C12N 15/117* | (2010.01) |
| *A61K 39/39* | (2006.01) |

(52) U.S. Cl.
CPC ........ *A61K 39/292* (2013.01); *A61K 31/7028* (2013.01); *A61K 38/204* (2013.01); *A61K 38/208* (2013.01); *A61K 39/0011* (2013.01); *A61K 39/39* (2013.01); *A61K 47/46* (2013.01); *C12N 7/00* (2013.01); *C12N 15/117* (2013.01); *A61K 2039/52* (2013.01); *A61K 2039/521* (2013.01); *A61K 2039/55516* (2013.01); *A61K 2039/55561* (2013.01); *A61K 2039/55572* (2013.01); *A61K 2039/64* (2013.01); *C12N 2310/17* (2013.01); *C12N 2320/31* (2013.01); *C12N 2730/10134* (2013.01)

(58) Field of Classification Search
CPC ...................................................... A61K 39/00
USPC .............................. 424/9.1, 9.2, 184.1, 234.1
See application file for complete search history.

(56) References Cited

FOREIGN PATENT DOCUMENTS

| | | |
|---|---|---|
| CN | 104758944 A | 7/2015 |
| WO | 2014036345 A2 | 3/2014 |
| WO | WO2014/036345 * | 3/2014 |

OTHER PUBLICATIONS

Patent Cooperation Treaty (PCT), International Search Report and Written Opinion for Application PCT/CN2015/094878 filed on Nov. 18, 2015, dated Feb. 25, 2016, International Searching Authority, CN.
Ni, D. et al., "Amphiphilic Hollow Carbonaceous Microspheres with Permeable Shells." Angew. Chem. Int. Ed. vol. 49 2010. pp. 4423-4227.

* cited by examiner

*Primary Examiner* — Rodney P Swartz
(74) *Attorney, Agent, or Firm* — McDonald Hopkins LLC

(57) ABSTRACT

The present invention provides a vaccine formulation, a preparation method therefor and a use thereof. The vaccine formulation comprises a vaccine carrier and an antigen component, wherein the vaccine carrier is obtained by hydrothermal transformation of microorganisms. The vaccine formulation of the present invention is obtained by compounding the vaccine carrier obtained by hydrothermal transformation of microorganisms with the antigen component.

17 Claims, 5 Drawing Sheets

VACCINE FORMULATION, PREPARATION METHOD THEREFOR AND USE THEREOF

CROSS-REFERENCE TO RELATED APPLICATION

This application is a 35 U.S.C. 371 national stage filing of PCT Application No. PCT/CN2015/094878 filed on Nov. 18, 2015, which claims priority to Chinese Patent Application No. 201510152994.3, filed on Apr. 2, 2015, each of which are incorporated herein in their entirety by reference.

TECHNICAL FIELD

The present invention pertains to the field of vaccine formulation, in particular to a vaccine formulation, preparation method therefor and use thereof.

BACKGROUND

In the development history of vaccines, the vaccine emerged initially was prepared by using attenuated or inactivated pathogenic organisms such as bacteria, viruses, *rickettsia* and the like. Vaccine formulations obtained in this way have potential biosafety issues in clinical applications, such as causing severe inflammatory and pathogenic viral infections. A purified or recombinant subunit antigen is usually used to replace the complete pathogenic organism in current vaccine formulations, which eliminates the possibility of pathogenic recurrence of the pathogen so that the biosafety of the vaccine in use has been greatly improved. However, protein or polypeptide subunit antigens are susceptible to degradation and are difficult to be uptaken by antigen presenting cells (APCs) compared to intact pathogenic microorganisms. More importantly, the "dangerous signal" post vaccination is deficient due to the lack of pathogen-associated molecular pattern (PAMP), and therefore APCs cannot be effectively activated. These problems make it difficult to obtain a strong immunogenicity when using subunit antigens alone, resulting in an unsatisfactory effect of immune response.

Studies on mechanisms of acquired immunity have shown that although pathogen antigens are important for immune recognition and immune memory, other characteristic components than the antigens in the pathogen also play a significant role in immune response. In the process of interacting with pathogens, the unique morphology, surface biological properties and various secreted biological signals of the pathogen can promote immune-related cells to approach, recognize and phagocytize pathogen components including antigenic components; and in the meanwhile, the PAMP in the pathogen components, upon contacting with or being uptaken by immune-related cells, can effectively activate these cells and induce a high level immune response. The body's immune system can effectively recognize and respond to the pathogens, precisely because they have such a series of important characteristics.

Inspired by this, some researchers have begun to try to develop vaccine formulations with characteristics of pathogens and have achieved some initial success. Take the most successful virosome as an example, it got its name for the imitation of key physiological structure and morphology of virus. Virosome is a class of special liposomes prepared by embedding the functional proteins located on the surface of the virus into the bilayer of liposomes. Envelope proteins of viruses including influenza virus, vesicular stomatitis virus and newcastle disease virus and the like, have been successfully used for the preparation of virosome. Like virus, virosome has a membrane fusion capacity by using the functional viral protein embedded in its lipid layer, and thus can simulate the process of viral infection of the animal body. More importantly, since only a small amount of virus protein with low toxicity is used without involving its genetic substance, virosome obtains a cell invasion ability similar to the virus while avoiding the biosafety issues during the use of live vaccines. To date, two virosome-based vaccines used for human have been marketed in 29 countries. At present, the virosome application is mainly limited to that there are great limitations on antigen loading, and the molecular size and the hydrophobic-hydrophilic properties of antigen are strictly required, and the loading efficiency is also need to be improved.

Although the bionic vaccine formulations represented by virosome are still in the early stages of development, and there are still a variety of deficiencies, the success that has been achieved showed the potential advantages and great development space of the vaccine formulations constructed by imitating pathogens.

Therefore, if a vaccine formulation with similar ability to pathogens in each process including APC uptake, antigen presentation and immune activation can be developed, it is expected to provide an effective solution for the prevention and treatment of many major diseases.

SUMMARY OF THE INVENTION

In view of the deficiencies of the prior art, the object of the present invention is to provide a vaccine formulation, preparation method and use thereof.

The present invention adopts the following technical scheme to achieve the object:

In one aspect, the present invention provides a vaccine formulation comprising a vaccine carrier and an antigen component, wherein the vaccine carrier is obtained by subjecting a microorganism to a hydrothermal transformation.

The present invention utilizes a hydrothermal synthesis method which is simple and easily industrialized, to bring the reaction environment to a subcritical or supercritical state by heating the aqueous solution in a confined space. In this case, the reaction is at a molecular level and the reaction efficiency is extremely high, thereby converting the microbial template material into a vaccine carrier. Properties of the obtained vaccine carrier material, such as porosity, hydrophobic-hydrophilic properties and density of surface immune-related ligand, are controlled by the hydrothermal reaction, and whereby the subsequent loading of the antigenic component can be effectively controlled. Compared with the attenuated and inactivated vaccines which use the pathogen microorganism as raw material similarly, the invention can not only ensure the safety of the vaccine in use completely, but also regulate the biological properties of the microbiological surface by the hydrothermal process, and further enhance the related immune activation ability.

Preferably, the microorganism is a pathogenic or non-pathogenic microorganism.

Preferably, the microorganism is any one selected from the group consisting of bacteria, fungus or virus.

Preferably, the microorganism is, but not limited to, any one selected from the group consisting of *Lactobacillus casei, Bifidobacterium, Mycobacterium, Staphylococcus, Lactococcus, Vibrio parahaemolyticus*, yeast or adenovirus, in terms of genus or species.

In the vaccine formulation according to the present invention, the vaccine carrier retains the morphological characteristics of the microorganism as a template and can promote rapid recognition and uptake of the vaccine carrier and its loaded antigen by antigen presenting cells.

Preferably, the vaccine carrier retains the immune-related surface ligands of the microorganism as a template.

Preferably, the surface ligands include, but not limited to, any one or at least two selected from the group consisting of membrane polysaccharide, mannose, N-acetylglucosamine, trehalose or lipoprotein.

This surface feature of the vaccine carrier can promote immune cell activation and regulate the intracellular transport and presentation of antigens, thereby effectively enhancing the level of immune response after vaccination.

In the vaccine formulation according to the present invention, the antigen component is any one or a combination of at least two selected from the group consisting of antigen protein, epitope peptide, and plasmid DNA or mRNA encoding antigen.

For example, when the vaccine formulation is used for immunoprophylaxis or immunotherapy against a particular malignant tumor, the antigenic component contained in the vaccine formulation may be one or more related or specific antigen(s) of this tumor, or may be plasmid DNA or mRNA carrying the coding information of these antigens; when the vaccine formulation is used for immunoprophylaxis or immunotherapy against an infectious disease, the antigen contained in the vaccine formulation may be one or more specific antigen protein(s) of the corresponding pathogenic microorganism, and may also be plasmid DNA or mRNA carrying the coding information of these antigens.

In another aspect, the present invention provides a preparation method of the vaccine formulation, comprising compounding the vaccine carrier obtained by subjecting a microorganism to a hydrothermal transformation with an antigen component to form the vaccine formulation.

The preparation method of the vaccine formulation according to the present invention comprises the following steps:

(a) a suspension of the microorganism is subjected to a hydrothermal reaction, and then the resultant is washed and dried to obtain a vaccine carrier;

(b) the vaccine carrier obtained in step (a) is compounded with the antigen component to obtain the vaccine formulation.

In the preparation method of the vaccine formulation according to the present invention, the solvent used in the hydrothermal reaction in step (a) is aqueous solution of any one or at least two selected from the group consisting of hydrochloric acid, sulfuric acid, nitric acid, acetic acid, sodium chloride, potassium chloride, potassium acetate, ethanol, acetaldehyde or glutaraldehyde.

Preferably, the concentration of the aqueous solution is 0.001-1.000 mol/L, for example, 0.001 mol/L, 0.002 mol/L, 0.004 mol/L, 0.008 mol/L, 0.010 mol/L, 0.015 mol/L, 0.018 mol/L, 0.020 mol/L, 0.024 mol/L, mol/L, 0.028 mol/L, 0.030 mol/L, 0.040 mol/L, 0.060 mol/L, 0.080 mol/L, 0.100 mol/L, 0.150 mol/L, 0.200 mol/L, 0.250 mol/L, 0.300 mol/L, 0.350 mol/L, 0.40 mol/L, 0.450 mol/L, 0.500 mol/L, 0.550 mol/L, 0.600 mol/L, 0.700 mol/L, 0.800 mol/L, 0.900 mol/L or 1.000 mol/L.

Preferably, the suspension of the microorganism in step (a) is a suspension prepared by adding the microorganism into the above solvent.

In the preparation method of the vaccine formulation according to the present invention, the hydrothermal reaction in step (a) is carried out by transferring the suspension in the step (a) into a hydrothermal reactor and then placing the hydrothermal reactor in a thermostatic chamber for heating at a constant temperature.

Preferably, the hydrothermal reaction in step (a) is performed at a temperature of 100-400° C., for example, 100° C., 110° C., 120° C., 140° C., 160° C., 180° C., 200° C., 220° C., 240° C., 260° C., 280° C., 300° C., 320° C., 340° C., 360° C., 380° C., 390° C. or 400° C., preferably 120-240° C.

Preferably, the hydrothermal reaction in step (a) is performed at a pressure of 1-3 MPa, for example, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa or 3 MPa.

Preferably, the hydrothermal reaction in step (a) is performed for 0.5-72 hours, for example 0.5 hours, 1 hour, 2 hours, 3 hours, 4 hours, 5 hours, 6 hours, 7 hours, 8 hours, 9 hours, 10 hours, 11 hours, 12 hours, 14 hours, 16 hours, 18 hours, 20 hours, 23 hours, 25 hours, 28 hours, 30 hours, 33 hours, 36 hours, 40 hours, 45 hours, 50 hours, 55 hours, 60 hours, 65 hours, 70 hours, 71 hours or 72 hours, preferably 2-12 hours, and further preferably 8-12 hours.

Preferably, the washing in step (a) is carried out with pure water, and the drying is freeze-drying.

In the preparation method of the vaccine formulation according to the present invention, the step (b) further comprises compounding the vaccine formulation with an immunomodulator.

Preferably, the immunomodulator is a biogenic immunomodulator or a non-biogenic immunomodulator.

Preferably, the immunomodulator is any one or a combination of at least two selected from the group consisting of unmethylated cytosine-guanosine motif, monophosphoryl lipid A, interleukin-2 or interleukin-12.

Preferably, the compounding in step (b) is carried out in a manner of adsorption, encapsulation or blending.

In a preferred embodiment, the preparation method of the vaccine formulation according to the present invention comprises the following steps:

(a) a suspension of the microorganism is transferred into a hydrothermal reactor, in which the hydrothermal reaction is carried out for 2-12 hours, at a temperature of 120-240° C., under a pressure of 1-3 MPa, and the resultant is washed with pure water and freeze-dried to obtain a vaccine carrier;

(b) the vaccine carrier obtained in step (a) is compounded with an antigen component and an immunomodulator to obtain the vaccine formulation.

The microorganism used in the vaccine carrier preparation of the invention has wide applicability, and encompasses various kinds of microorganisms such as bacteria, fungus or virus; there are also many options for the species of antigen and immunomodulator with which the vaccine carrier can be compounded; when implementing the technical solution of the invention, vaccines against different diseases can be constructed by selecting different antigens, and therefore the technical solution of the invention is universally applicable for vaccine construction.

In another aspect, the present invention provides the use of the vaccine formulation in the manufacture of a medicament for the prevention or treatment of a malignant tumor or an infectious disease.

Preferably, the infectious disease is any one selected from the group consisting of hepatitis B, influenza, bacterial pneumonia, or bacillary dysentery.

The vaccine formulation provided by the present invention can achieve a strong immune activation effect and effectively enhance the immunogenicity of the loaded antigen by simulating the characteristic morphology, surface ligand and the molecular signal of the pathogen. Immunotherapy and immunoprophylaxis against a specific disease can be achieved, through the body's specific immune response to the antigen.

The invention has the following beneficial effects compared with the prior art:

According to the present invention, the vaccine formulation is obtained through compounding the vaccine carrier prepared by subjecting the microorganism as template raw material to a hydrothermal reaction with an antigen component and, optionally, an immunomodulator. The properties of the vaccine carrier material such as porosity, hydrophobic-hydrophilic properties, and immune-related surface ligand density have been optimized, so that when compounding the vaccine carrier with an antigen component and, optionally, an immunomodulator, the antigen loading efficiency is improved, the prepared vaccine formulation has achieved a strong immune activation effect, the immunogenicity of the loaded antigen is effectively enhanced, and immunotherapy and immunoprophylaxis against a specific disease have been achieved through the specific immune response to the antigen formed by the body.

DETAILED DESCRIPTION

The technical solution of the present invention will be further illustrated below by specific embodiments. It will be apparent to those skilled in the art that the embodiments are merely illustrative of the invention and should not be construed as limiting the invention in particular.

Example 1

In the present example, a vaccine carrier was prepared by the following procedure:

A microorganism suspension was prepared by dispersing 5 g *Lactobacillus casei* bacteria mire cultured artificially into 100 mL 0.01 mol/L hydrochloric acid solution, then transferred into a hydrothermal reactor placed in a thermostatic chamber, maintained at a pressure of 3 MPa and heated for 10 hours at a constant temperature of 180° C., and then the resulting precipitate was washed with pure water and freeze-dried to obtain a vaccine carrier (DB). The term "bacteria mire" refers to the bacteria pellet collected by centrifugation. The term "cultured artificially" means bacteria cultured in nutrient broth at 37° C.

Figure 1:
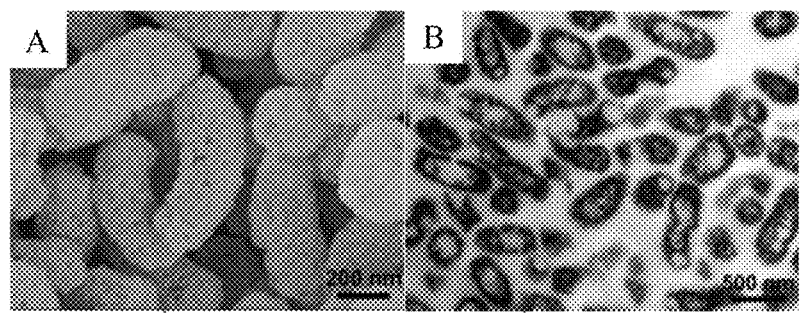
FIG. 1 shows a scanning electron microscope image (A) and a transmission electron microscope image (B) of the vaccine carrier prepared in Example 1.

The prepared vaccine carrier was characterized by scanning electron microscope (JEOL, JSM-6700F) and transmission electron microscope (JEOL, JEM-1400). As shown in FIG. 1, the prepared vaccine carrier retained the morphological characteristics of the bacilli. In addition, porous microstructures with an average pore size of 27.66 nm were formed on the surface of the carrier by means of the violent hydrolysis reaction in the acidic solvent environment.

Example 2

In the present example, a vaccine carrier was prepared by the following procedure:

A microorganism suspension was prepared by dispersing 2 g *Lactobacillus casei* bacteria mire cultured artificially into 100 mL 0.1 mol/L hydrochloric acid solution, then transferred into a hydrothermal reactor placed in a thermostatic chamber, maintained at a pressure of 2 MPa and heated for 12 hours at a constant temperature of 200° C., and then the resulting precipitate was washed with pure water and freeze-dried to obtain a vaccine carrier.

Figure 2:
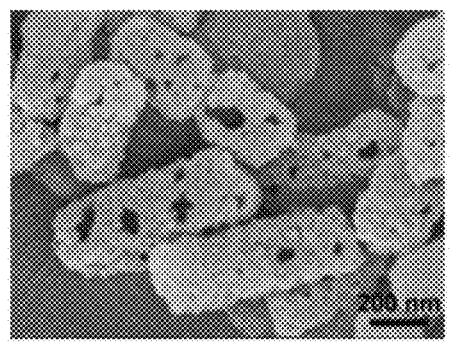
FIG. 2 shows a scanning electron microscope image of the vaccine carrier prepared in Example 2.

The prepared vaccine carrier was characterized by scanning electron microscope. As shown in FIG. 2, a large number of macroporous structures were formed on the surface of the carrier material due to the hydrothermal reaction in the acidic solvent environment.

Example 3

In the present example, a vaccine carrier was prepared by the following procedure:

A microorganism suspension was prepared by dispersing 5 g *Lactobacillus casei* bacteria mire cultured artificially into 100 mL 0.01 mol/L hydrochloric acid solution, then transferred into a hydrothermal reactor placed in a thermostatic chamber, maintained at a pressure of 3 MPa and heated for 72 hours at a constant temperature of 100° C., and then the resulting precipitate was washed with pure water and freeze-dried to obtain a vaccine carrier.

Example 4

In the present example, a vaccine carrier was prepared by the following procedure:

10 g artificially cultured *vibrio parahaemolyticus* bacteria mire was dispersed into 50 mL 1.00% (v/v) glutaraldehyde solution, the resultant was transferred into a hydrothermal reactor placed in a thermostatic chamber, maintained at a pressure of 1 MPa and heated for 2 hours at a constant temperature of 250° C., and then the resulting precipitate was washed with pure water and freeze-dried to obtain a vaccine carrier.

Figure 3:
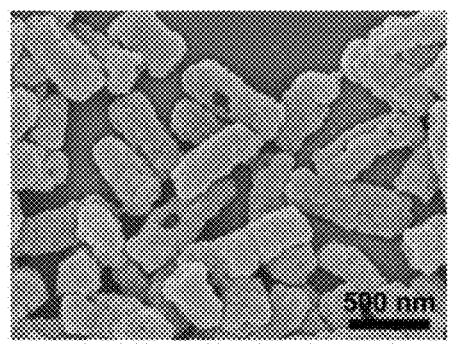
FIG. 3 shows a scanning electron microscope image of the vaccine carrier prepared in Example 4.

The prepared vaccine carrier was characterized by scanning electron microscope. As shown in FIG. 3, a large number of macroporous structures were formed on the surface of the carrier material due to the hydrothermal reaction.

Example 5

In the present example, a vaccine carrier was prepared by the following procedure:

10 g artificially cultured *Vibrio parahaemolyticus* bacteria mire was dispersed into 50 mL 1.00% (v/v) glutaraldehyde solution, the resultant was transferred into a hydrothermal reactor placed in a thermostatic chamber, maintained at a pressure of 1 MPa and heated for 0.5 hours at a constant temperature of 400° C., and the resulting precipitate was washed with pure water and freeze-dried to obtain a vaccine carrier.

Example 6

In the present example, a vaccine carrier was prepared by the following procedure:

10 g artificially cultured *Streptococcus thermophilus* bacteria mire was dispersed into 50 mL 0.05 g/mL sodium chloride solution, the resultant was transferred into a hydrothermal reactor placed in a thermostatic chamber, heated for 0.5 hours at a constant temperature of 180° C., and the resulting precipitate was washed with pure water and freeze-dried to obtain a vaccine carrier.

Figure 4:
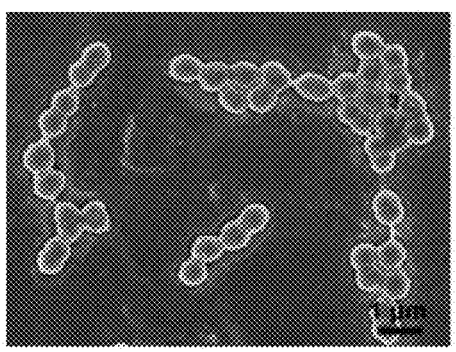
FIG. 4 shows a scanning electron microscope image of the vaccine carrier prepared in Example 6.

The prepared vaccine carrier was characterized by scanning electron microscope. As shown in FIG. 4, the vaccine carrier prepared by hydrothermal treatment retained the spherical individual morphology of *Streptococcus thermophilus*, and also retained the structural characteristic of the individuals interlinking with each other.

Example 7

In the present example, a vaccine carrier was prepared by the following procedure:

10 g artificially cultured *Pediococcus acidilactici* bacteria mire was dispersed into 50 mL 0.1 mol/mL ethanol solution, the resultant was transferred into a hydrothermal reactor placed in a thermostatic chamber, heated for 72 hours at a constant temperature of 150° C., and the resulting precipitate was washed with pure water and freeze-dried to obtain a vaccine carrier.

Figure 5:
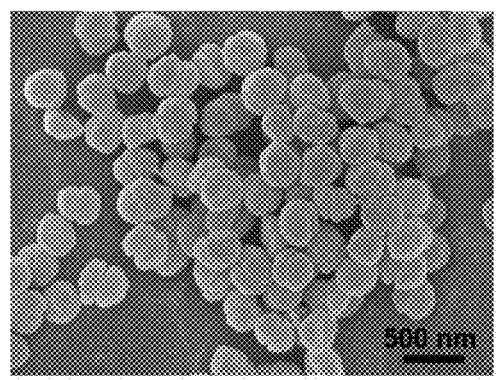
FIG. 5 shows a scanning electron microscope image of the vaccine carrier prepared in Example 7.

The prepared vaccine carrier was characterized by scanning electron microscope. As shown in FIG. 5, the vaccine carrier prepared by hydrothermal treatment completely retained the oblate spherically morphological characteristics of *Pediococcus acidilactici*.

Example 8

In the present example, a vaccine carrier was prepared by the following procedure:

10 g artificially cultured Yeast bacteria mire was dispersed into 50 mL 0.001 mol/mL sodium chloride solution, the resultant was transferred into a hydrothermal reactor placed in a thermostatic chamber, heated for 24 hours at a constant temperature of 300° C., and the resulting precipitate was washed with pure water and freeze-dried to obtain a vaccine carrier.

Example 9

In the present example, the binding ability of the vaccine carrier to the mannose receptor was tested by the following procedure:

The vaccine carrier (50 μg) prepared using different hydrothermal treatment times of 0 h, 4 h, 8 h, 12 h, 24 h, 48 h and 72 h (other conditions and operating procedures were the same as Example 1) according to the procedure of Example 1 was blocked beforehand with bovine serum albumin blocking solution in order to avoid non-specific action with the mannose receptor in subsequent steps, and the blocked vaccine carrier was then blended with 20 μg mannose receptor and incubated at 4° C. for 10 h.

The mannose receptors bound to the vaccine carrier were labeled with fluorescently modified anti-CD206 antibody and the fluorescence intensity was quantified by flow cytometry (Becton Dickinson, CyAn™ ADP). The relative binding capacity of the vaccine carrier prepared using different hydrothermal treatment times to mannose receptors was determined, as shown in FIG. 6.

Figure 6:
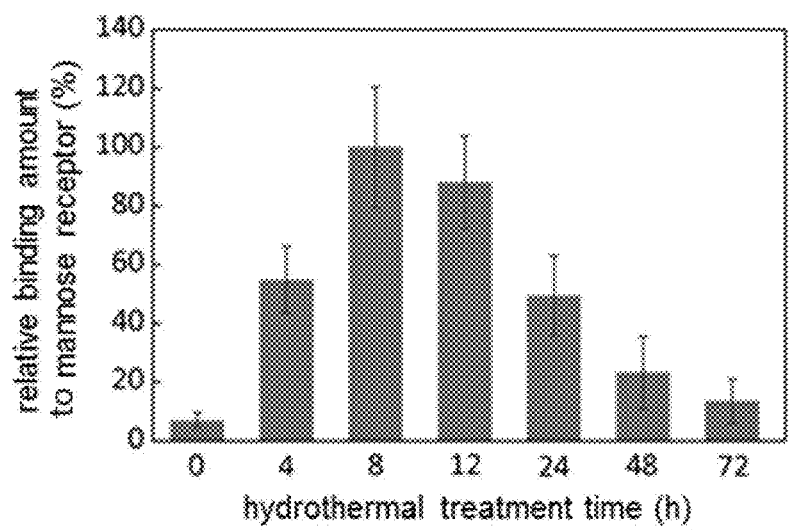
FIG. 6 is a graph comparing the binding ability of vaccine carriers prepared with different hydrothermal reaction times in Example 9 to the mannose receptor.

It can be seen from FIG. 6 that the relative binding amount of the vaccine carrier to the mannose receptor increased with the continuous progress of the hydrothermal reaction. As the hydrothermal reaction progressed, the mannose ligands located on the surface of *Lactobacillus casei* were gradually exposed to show an admirable binding capacity with mannose receptor. However, the mannose ligands located on the surface of *Lactobacillus casei* were gradually destroyed as the hydrothermal time prolonged when the treating time exceeded 12 h, resulting in a continued decrease in binding ability with mannose receptors.

Example 10

In the present example, a vaccine formulation was prepared by the following procedure:

100 μg vaccine carrier prepared in Example 1 was blended with 1 mL solution containing 75 μg/mL of CpG 1862 and 1 mL 20 μg/mL of OVA at 4° C. for 2 hours, centrifuged to obtain a vaccine formulation loaded with CpG and OVA. It was measured that the loading of CpG was 1.7 wt % and the loading of OVA was 5.3 wt %.

Example 11

In the present example, a vaccine formulation was prepared by the following procedure:

100 μg vaccine carrier prepared in Example 1 was blended with 1 mL solution containing 150 μg/mL CpG 1862 and 80 μg/mL OVA at 4° C. for 2 hours, centrifuged to obtain a vaccine formulation loaded with CpG and OVA. It was measured that the loading of CpG was 4 wt % and the loading of OVA was 40 wt %.

Example 12

In the present example, a vaccine formulation was prepared by the following procedure:

100 μg vaccine carrier prepared in Example 1 was blended with 1 mL solution containing 300 μg/mL CpG 1862 and 200 μg/mL OVA at 4° C. for 2 hours, centrifuged to obtain a vaccine formulation loaded with CpG and OVA.

It was measured that the loading of CpG was 8 wt % and the loading of OVA was 85.2 wt %.

Example 13

In the present example, a vaccine formulation was prepared by the following procedure:

100 μg vaccine carrier prepared in Example 1 was blended with 1 mL 120 μg/mL CpG 1862 at 4° C. for 2 hours, centrifuged to obtain a vaccine carrier loaded with CpG. Subsequently, the vaccine carrier loaded with CpG was blended with 1 mL 100 μg/mL whole-cell antigen, which was extracted from mouse breast cancer 4T1 cell line, at 4° C. for 2 hours, centrifuged to obtain a vaccine formulation against 4T1 breast cancer. It was measured that the loading of CpG was about 4.0 wt % and the loading of whole-cell antigen was 40 wt %.

Example 14

In the present example, a vaccine formulation was prepared by the following procedure:

100 μg vaccine carrier prepared in Example 2 was blended with 1 mL 20 μg/mL IL-12 at 4° C. for 2 hours, centrifuged to obtain a vaccine carrier loaded with IL-12. Subsequently, the vaccine carrier loaded with IL-12 was blended with 1 mL 100 μg/mL hepatitis B surface antigen (HBsAg) at 4° C. for 2 hours, centrifuged to obtain a vaccine formulation against hepatitis B. It was measured that the loading of IL-2 was 3.1 wt % and the loading of HBsAg was 13.5 wt %.

Example 15

In the present example, the vaccine formulation was subjected to an in vitro antigen presenting cell activation assay by the following method:

Vaccine formulation prepared in Example 11 was incubated with dendritic cells (the major specialized antigen-presenting cells) for 24 hours (with an OVA concentration of 1 μg/mL). The activation effect of the vaccine formulation (DB:CpG/OVA) on dendritic cells was determined, with PBS group, OVA group, CpG blank group (DB:OVA), vaccine carrier blank group (CpG+OVA) as well as 100 ng/mL lipopolysaccharide group set as control groups, and the OVA concentration being 1 μg/mL in each group. The indicators including T cell recognition signals SIINFEKL-MHC I, MHC II and co-stimulatory signals CD40, CD80 and CD86 expressed on the surface of dendritic cells; immune-promoting cytokines secreted extracellularly such as tumor necrosis factor α (TNF-α), interferon-γ (IFN-γ), interleukin-6 (IL-6), interleukin-12 (IL-12) as well as monocyte chemoattractant protein-1 (MCP-1) were determined, and the results were shown in FIG. 7.

Figure 7:
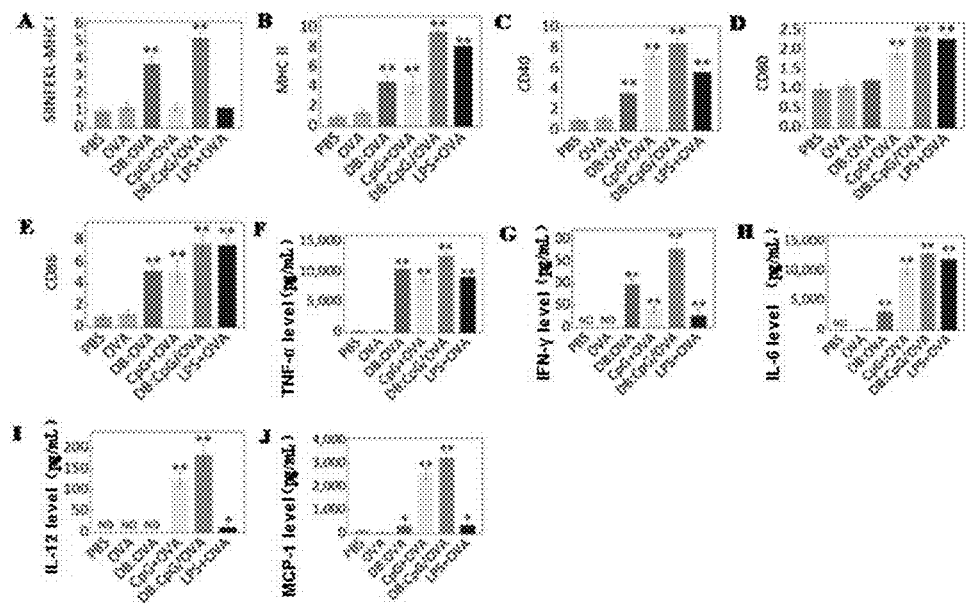
FIG. 7 is a graph showing the expression levels of various surface signals (A-E) and secretion levels of cytokines (F-J) of dendritic cells in Example 15.

It can be seen from FIG. 7 that the vaccine formulation group (DB: CpG/OVA) can effectively activate the dendritic cells, and the above indicators have been greatly improved, compared with each control group. This indicates that the vaccine formulation has an effective immune activation effect.

Example 16

In the present example, the vaccine formulation was subjected to an in vivo antigen specific CD8 T cell proliferation assay by the following method:

Male C57BL/6 mice aged 6-8 weeks were subjected to venous re-transfusion with OVA-specific CD8 T cells, 12 hours ahead of time. Subsequently, mice were subcutaneously immunized with the vaccine formulation (DB:CpG/OVA, containing 20 μg OVA, 50 μg vaccine carrier and 2 μg CpG) prepared in Example 11, with PBS, OVA, DB: OVA and CpG+OVA groups as control groups, and each mouse was inoculated with 100 μL sample of each group.

After 72 hours, the mice lymph nodes and spleen cells were extracted and the proliferation ratio of OVA-specific CD8 T cells was analyzed by flow cytometry. The results showed that the average proliferation ratio of OVA-specific CD8 T cells in mice of vaccine formulation (DB:CpG/OVA) group was up to 94.8%, while that of OVA group was only 13.4%. This indicates that the prepared vaccine formulation has achieved the ultimately effective immune activation and enhanced the immunogenicity of the antigen.

Example 17

In the present example, the vaccine formulation was subjected to an in vivo CD8 T cell activation assay by the following method:

Male C57BL/6 mice aged 6-8 weeks were subcutaneously immunized with 100 μL of the vaccine formulation prepared in Example 11. The control groups were set as in Example 16. After 28 days, mice spleen cells were extracted and the percentage of CD8 T cells secreting IFN-γ was analyzed by flow cytometry. In addition, spleen cells of mice in each group were incubated with OVA-expressing lymphoma cells E. G7 (lymphoma cells EL-4 which do not express OVA were used as control) at a ratio of 5:1, 10:1 and 20:1 (the ratio of effector cells to target cells) for 12 hours, and the ability to kill E.G7 cells was evaluated by determining the leakage level of lactate dehydrogenase. The results were shown as FIG. 8 and FIG. 9.

Figure 8:
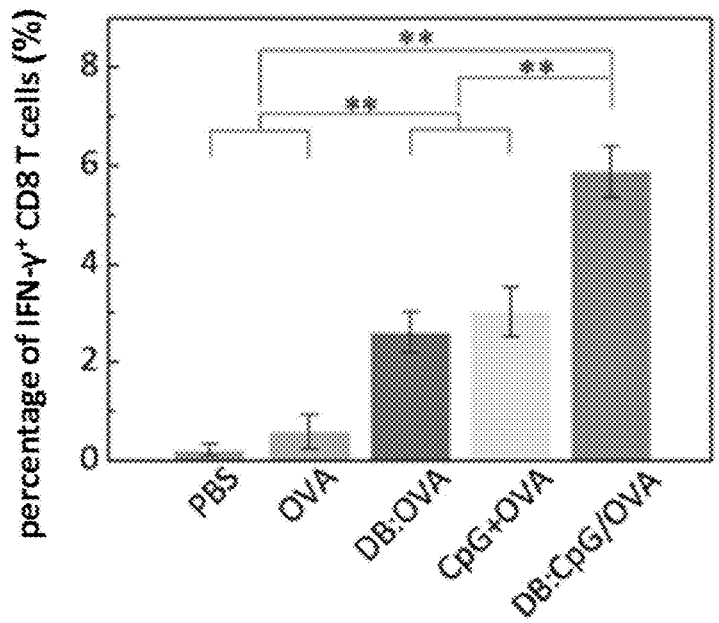
FIG. 8 is a graph showing the percentage of IFN-γ+CD8 T cells in spleen cells of mice in each group in Example 17.
Figure 9:
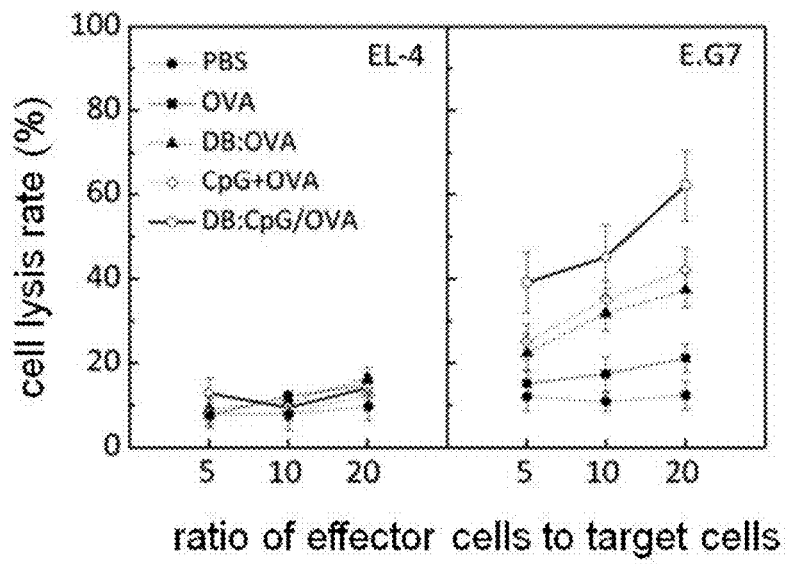
FIG. 9 is a graph showing the cleavage rate of lymphoma cells of mice in each group in Example 17.

It can be seen from FIG. 8 that the percentage of IFN-γ-positive CD8 T cells having the ability to kill target cells in the spleen cells of mice immunized with the vaccine preparation were significantly increased, i.e., the CD8 T cells were effectively activated. It can be seen from FIG. 9 that the cell lysis rate for the group of lymphoma cells E.G7 was significantly higher than that for the control group of lymphoma cells EL-4 which do not express OVA, indicating that the group administrated with the vaccine formulation shows the actually strongest ability to killing the target tumor cells.

Example 18

In the present example, the vaccine formulation was subjected to immunotherapy assay of a malignant tumor by the following method:

Male C 57BL/6 mice aged 6-8 weeks were inoculated with E.G7 tumor cells ($5 \times 10^6$ cells per mouse) on day 0, and then immunized subcutaneously with 100 μL of the vaccine formulation prepared in Example 11 when the tumor volume reached the size of 0.5 cm×0.5 cm×0.5 cm on day 7. Among the vaccine formulation group, a boost immunization group (2×DB: CpG/OVA) which received a secondary enhanced immunization was further set, wherein the enhanced vaccination was performed on day 14. The control groups were set as in Example 16, and additionally the mice inoculated with attenuated *Listeria monocytogenes* (lm-OVA) were set as positive control group. The tumor volume and survival time of the mice were then recorded and the results were shown in FIG. 10.

Figure 10:
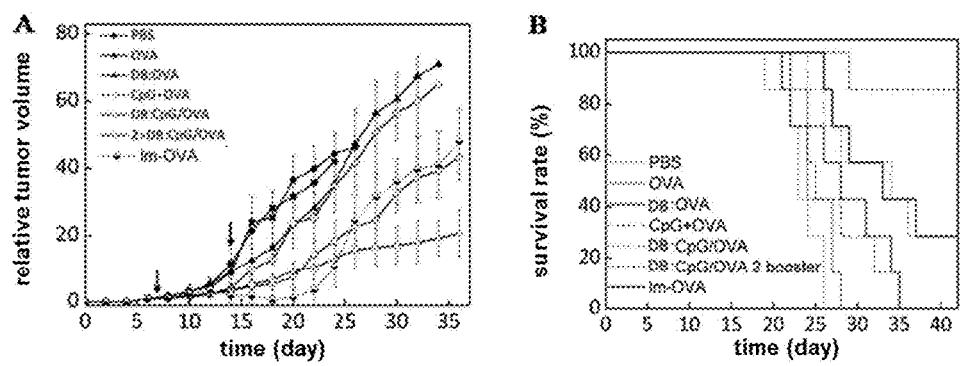
FIG. 10 is a graph showing the tumor growth curve (A) and the survival time (B) of mice in each group in Example 18.

It can be seen from FIG. 10 that the group inoculated with the vaccine formulation was able to obtain a tumor growth inhibitory effect comparable to that of the group inoculated with attenuated *Listeria monocytogenes* (lm-OVA), significantly reduced the tumor volume of the mice, and in addition, the secondary enhanced immunization treatment with the vaccine formulation can effectively delay tumor growth and prolong the average survival time of mice.

Example 19

In the present example, the vaccine formulation was subjected to early immunotherapy assay of a malignant tumor by the following method:

Male C57BL/6 mice aged 6-8 weeks were inoculated with E.G7 tumor cells ($5 \times 10^6$ cells per mouse) on day 0, immunized subcutaneously with 100 μL of the vaccine formulation prepared in Example 11 on day 4 and subjected to an enhanced vaccine inoculation on day 11. PBS group and OVA group were set as control groups at the same time. The tumor volume and survival time of the mice were then recorded and the results were shown in FIG. 11.

Figure 11:
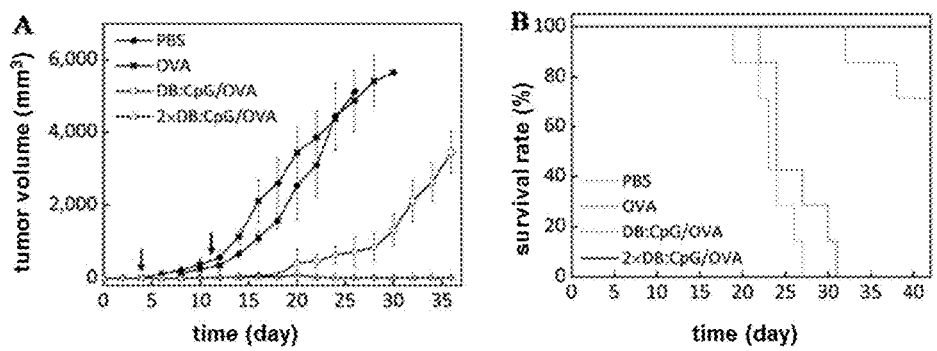
FIG. 11 is a graph showing the tumor growth curve (A) and the survival time (B) of mice in each group in Example 19.

It can be seen from FIG. 11 that the secondary enhanced immunization treatment with the vaccine formulation can completely prevent tumor growth and greatly guarantee the survival rate of the mice.

Example 20

In the present example, the vaccine formulation was subjected to immunotherapy assay of a malignant tumor by the following method:

Female BALB/c mice aged 6-8 weeks were subjected to breast pad orthotopic implantation with 4T1 tumor cells ($5 \times 10^6$ cells per mouse) on day 0, each mouse was vaccinated with 100 μL of the vaccine formulation (containing 20 μg whole-cell antigen, 50 μg vaccine carrier and 2 μg CpG) prepared in Example 13 when the tumor volume reached the size of 0.5 cm×0.5 cm×0.5 cm on day 7. The tumor volume and survival time of the mice were then recorded. The results showed that, upon the secondary enhanced immunization treatment with the vaccine formulation, the tumor growth was effectively delayed and the average survival time of the mice, which was 63.8 days, was significantly increased over the PBS group, which was 46.3 days.

Example 21

In the present example, the vaccine formulation was subjected to antigen-specific central memory cell differentiation assay by the following method:

Male C57BL/6 mice aged 6-8 weeks were immunized subcutaneously with 100 μL of the vaccine formulation prepared in Example 11. Mice lymph node cells were harvested on day 35 and the percentage of central memory cells in the population of OVA-specific CD8 T cells was determined. The results showed that the percentage of central memory T cells after the secondary immunization was 22.5%, compared with 2.6% for OVA immunized mice.

Example 22

In the present example, the vaccine formulation was subjected to antigen-specific antibody titer assay by the following method:

Male C57BL/6 mice aged 6-8 weeks were immunized subcutaneously with 100 μL of the vaccine formulation prepared in Example 11. Two treatment groups: primary immunization (DB:CpG/OVA) and secondary immunization (2×DB:CpG/OVA) were set, and the group of OVA blended with 500 μg aluminum adjuvant as well as the group of OVA were set as control groups. Mice serum was harvested at days 14, 21, 28 and 35, and the titer level of OVA-specific IgG thereof was determined. The results were shown in FIG. 12.

Figure 12:
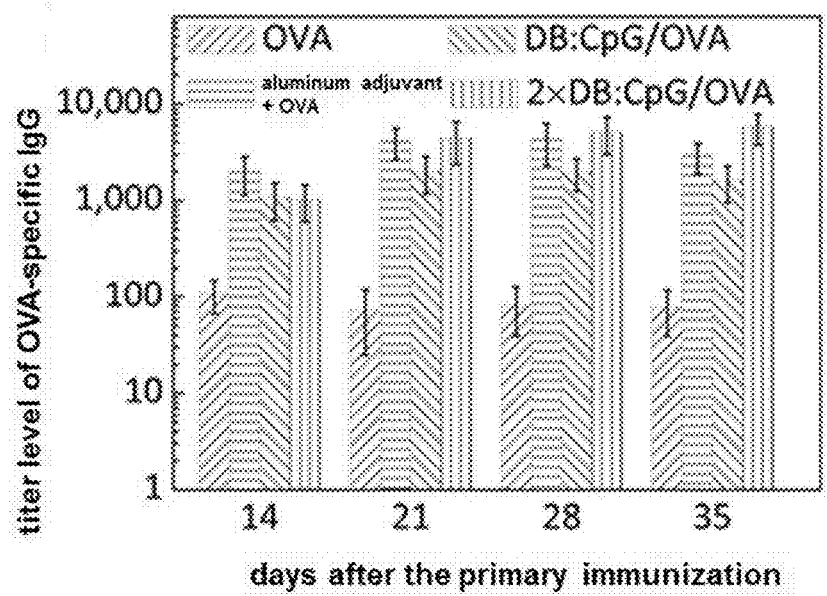
FIG. 12 is a graph showing the titer level of OVA-specific IgG of mice in each group at days 14, 21, 28 and 35 in Example 22.

It can be seen from FIG. 12 that the group of the secondary enhanced immunization with the vaccine formulation can achieve an OVA-specific IgG antibody expression level better than the aluminum adjuvant group, which effect is sustained and has reached or exceeded the level of the commercially available aluminum adjuvant.

Example 23

In the present example, the vaccine formulation against hepatitis B was subjected to antigen-specific antibody titer assay by the following method:

The effect of inducing antibody by the vaccine formulation against hepatitis B prepared in Example 14 was tested in the same procedure as in Example 21, in which female BALB/c mice were used as the test subject, and the group of OVA blended with 500 μg aluminum adjuvant was also set as control group.

The results showed that the vaccine formulation had a strong and sustained effect of inducing antigen-specific IgG antibody, wherein the antibody titer thereof was maintained at a high level of greater than 6000 from day 14 to day 35, while the average antibody titer of the commercially available aluminum adjuvant group was about 3700 during the same period.

Example 24

In the present example, the vaccine formulation was subjected to immunoprophylaxis and immunotherapy assay against a malignant tumor by the following method:

Male C57BL/6 mice aged 6-8 weeks were immunized subcutaneously with 100 μL of the vaccine formulation prepared in Example 11. Specifically, primary immunization (DB:CpG/OVA) and secondary immunization (2×DB: CpG/OVA) were performed on day 0 and day 7, respectively, and OVA group was used as control group. Each mouse was inoculated under the armpit with $1 \times 10^6$ E.G7 cells on day 21. Subsequently, the occurrence and development of the tumor were recorded, and the results were shown in FIG. 13.

Figure 13:
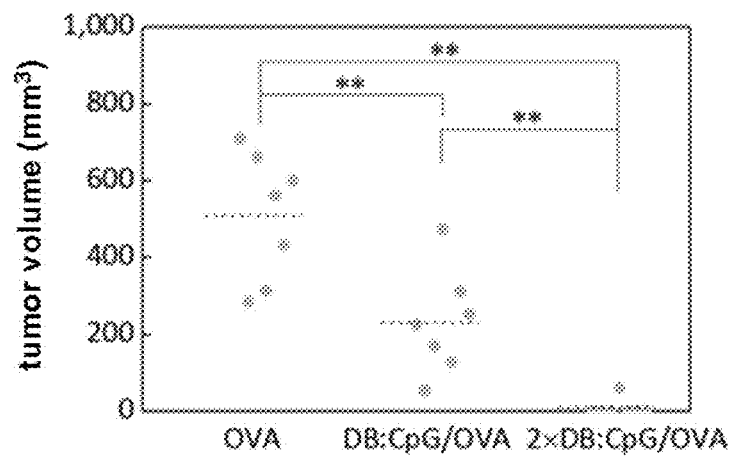
FIG. 13 is a graph showing the immunoprophylaxis and immunotherapy effect of vaccines in each group on malignant tumor in Example 24.

It can been seen from FIG. 13 that the tumor volume of mice in the primary immunization group immunized with the vaccine formulation (DB:CpG/OVA) was significantly smaller than that of the OVA group. In the secondary immunization group immunized with the vaccine formulation (2×DB: CpG/OVA), tumor burden, with small volume, was formed in only 1 of 7 mice, indicating that the vaccine formulation can have an immunoprophylaxis effect on malignant tumors.

Therefore, according to the present invention, the vaccine formulation is obtained through compounding the vaccine carrier prepared by subjecting the microorganism as template raw material to a hydrothermal reaction with an antigen component and, optionally, an immunomodulator. The properties of the vaccine carrier material such as porosity, hydrophobic-hydrophilic properties, and immune-related surface ligand density have been optimized, so that when compounding the vaccine carrier with an antigen component and, optionally, an immunomodulator, the antigen loading efficiency is improved, the prepared vaccine formulation has achieved a strong immune activation effect, the immunogenicity of the loaded antigen is effectively enhanced, and immunotherapy and immunoprophylaxis against a specific disease have been achieved through the specific immune response to the antigen formed by the body.

The applicant declares that the present invention illustrates the vaccine formulation, preparation method and use thereof according to the present invention by the above-described examples. However, the present invention is not limited to the above-described examples, i.e. it does not mean that the present invention must be carried out depending on the above-described examples. It will be apparent to those skilled in the art that any improvements to the present invention, equivalence of the materials selected for use in the present invention, addition of auxiliary ingredients, selection of specific ways, etc., are within the scope of the present invention and the scope of the disclosure.

The invention claimed is:

1. A vaccine formulation, which comprises a vaccine carrier and an antigen component, wherein the vaccine carrier is obtained by subjecting a microorganism to a hydrothermal transformation, wherein the hydrothermal transformation of the microorganism comprises: subjecting said microorganism to 100-400° C., at 1-3 MPa for 0.5-72 hours.

2. The vaccine formulation according to claim 1, wherein the microorganism is a pathogenic or non-pathogenic microorganism.

3. The vaccine formulation according to claim 1, wherein the vaccine carrier retains the morphological characteristics of the microorganism as a template.

4. The vaccine formulation according to claim 1, wherein the microorganism is any one selected from the group consisting of bacteria, fungus, or virus.

5. A preparation method of the vaccine formulation according to claim 1, comprising compounding the vaccine carrier obtained by subjecting a microorganism to a hydrothermal transformation with an antigen component to form the vaccine formulation, wherein the compounding is carried out in a manner of adsorption, encapsulation, or blending, and wherein the hydrothermal transformation of the microorganism comprises: subjecting said microorganism to 100-400° C., at 1-3 MPa for 0.5-72 hours.

6. The preparation method according to claim 5, comprising the following steps:
    (a) a suspension of the microorganism is subjected to a hydrothermal reaction, and then the resultant is washed and dried to obtain a vaccine carrier;
    (b) the vaccine carrier obtained in step (a) is compounded with the antigen component to obtain the vaccine formulation.

7. The preparation method according to claim 6, wherein the suspension of the microorganism in step (a) is aqueous solution of any one or at least two selected from the group consisting of hydrochloric acid, sulfuric acid, nitric acid, acetic acid, sodium chloride, potassium chloride, potassium acetate, ethanol, acetaldehyde, or glutaraldehyde as the solvent.

8. The preparation method according to claim 6, wherein the hydrothermal reaction in step (a) is carried out by transferring the suspension of the microorganism into a hydrothermal reactor and then placing the hydrothermal reactor in a thermostatic chamber for heating at a constant temperature.

9. The preparation method according to claim 6, wherein the step (b) further comprises compounding the vaccine formulation with an immunomodulator.

10. A method of preventing a patient from suffering a malignant tumor or an infectious disease or treating a patient with a malignant tumor or an infectious disease, comprising administrating prophylactically or therapeutically effective amount of the vaccine formulation according to claim 1 to the patient.

11. The vaccine formulation according to claim 1, wherein the microorganism is any one selected from the group consisting of *Lactobacillus casei, Bifidobacterium, Mycobacterium, Staphylococcus, Lactococcus, Vibrio parahaemolyticus*, Yeast, or adenovirus.

12. The vaccine formulation according to claim 1, wherein the vaccine carrier retains immune-related surface ligand of the microorganism as a template.

13. The vaccine formulation according to claim 12, wherein the immune-related surface ligand is any one or a combination of at least two selected from the group consisting of membrane polysaccharides, mannose, N-acetylglucosamine, trehalose or lipoprotein.

14. The preparation method according to claim 7, wherein the concentration of the aqueous solution is 0.001-1.000 mol/L.

15. The preparation method according to claim 9, wherein the immunomodulator is any one or a combination of at least two selected from the group consisting of unmethylated cytosine-guanosine motif, monophosphoryl lipid A, interleukin-2, or interleukin-12.

16. The preparation method according to claim 9, wherein the compounding in step (b) is carried out in a manner of adsorption, encapsulation, or blending.

17. The preparation method according to claim 10, wherein the infectious disease is any one selected from the group consisting of hepatitis B, influenza, bacterial pneumonia, or bacillary dysentery.

* * * * *